United States Patent
Strehl et al.

(10) Patent No.: US 8,526,691 B2
(45) Date of Patent: Sep. 3, 2013

(54) SYSTEM AND METHOD FOR PASSIVE MEDICAL DEVICE NAVIGATION UNDER REAL-TIME MRI GUIDANCE

(75) Inventors: Wilhelm Strehl, Nuremberg (DE); Wesley D. Gilson, Pasadena, MD (US); Eva Rothgang, Nürnberg (DE)

(73) Assignee: Siemens Aktiengesellschaft, München (DE)

( * ) Notice: Subject to any disclaimer, the term of this patent is extended or adjusted under 35 U.S.C. 154(b) by 258 days.

(21) Appl. No.: 13/150,384

(22) Filed: Jun. 1, 2011

(65) Prior Publication Data

US 2012/0089008 A1    Apr. 12, 2012

Related U.S. Application Data

(60) Provisional application No. 61/352,854, filed on Jun. 9, 2010.

(51) Int. Cl.
   *G06K 9/00* (2006.01)
   *G06K 9/40* (2006.01)

(52) U.S. Cl.
   USPC .......................................... 382/128; 382/254

(58) Field of Classification Search
   USPC .................................. 382/128–134, 254–275
   See application file for complete search history.

(56) References Cited

U.S. PATENT DOCUMENTS

| | | | |
|---|---|---|---|
| 5,715,822 | A | 2/1998 | Watkins et al. |
| 6,430,429 | B1 | 8/2002 | Van Vaals |
| 6,516,213 | B1 | 2/2003 | Nevo |
| 2007/0133898 | A1* | 6/2007 | Gemelos et al. .............. 382/275 |
| 2011/0007956 | A1* | 1/2011 | Meyer et al. .................. 382/131 |

OTHER PUBLICATIONS

L. Shapiro, G. Stockman: Computer Vision, Prentice Hall, 2001.

\* cited by examiner

*Primary Examiner* — Alex Liew
(74) *Attorney, Agent, or Firm* — Donald B. Paschburg; F. Chau & Associates, LLC

(57) ABSTRACT

A method for tracking a needle along a path under real-time magnetic resonance imaging (MRI) guidance includes extracting a candidate needle artifact region from a plurality of incoming MR images of a needle inside biological tissue, determining an initial needle direction vector from the candidate needle artifact region in each of the plurality of incoming needle images, determining an initial needle base point from an intersection of the needle direction vector with a first incoming needle image, and an initial needle tip point from an intersection of the needle direction vector with a last incoming needle image, and tracking said needle by minimizing a cost function of the initial base point and initial direction vector to calculate an updated base point and updated direction vector. The updated base point and direction vector are used to visualize the advance of the needle along the path through the biological tissue.

23 Claims, 11 Drawing Sheets

(a)     (b)

(a)                  (b)

| Region | 51 | 52 | 53 |
|---|---|---|---|
| Area | 52 | 54 | 34 |
| Perimeter | 23.3 | 33.5 | 29.8 |
| Circularity | 0.8 | 1.7 | 2.1 |

(a) (b)

| Insertion | Slice | Detected | Error [mm] | Error [°] |
|---|---|---|---|---|
| 1 | 1 | correct | 2.2 | 8.2 |
|   | 2 | correct | 1.6 |   |
|   | 3 | correct | 0.5 |   |
| 2 | 1 | correct | 1.2 | 16.3 |
|   | 2 | correct | 1.0 |   |
|   | 3 | correct | 2.8 |   |
| 3 | 1 | correct | 1.5 | 5.0 |
|   | 2 | correct | 1.1 |   |
|   | 3 | correct | 0.9 |   |
| 4 | 1 | correct | 2.7 | 11.4 |
|   | 2 | correct | 2.4 |   |
|   | 3 | correct | 2.9 |   |
| 5 | 1 | correct | 2.0 | 8.3 |
|   | 2 | correct | 2.8 |   |
|   | 3 | correct | 2.2 |   |
| 6 | 1 | correct | 3.7 | 2.3 |
|   | 2 | correct | 4.2 |   |
|   | 3 | correct | 3.7 |   |
| 7 | 1 | correct | 2.7 | 9.2 |
|   | 2 | correct | 4.4 |   |
|   | 3 | correct | 3.9 |   |
| 8 | 1 | correct | 2.2 | 5.9 |
|   | 2 | correct | 3.1 |   |
|   | 3 | correct | 2.8 |   |
| 9 | 1 | missed | N/A | 9.4 |
|   | 2 | correct | 5.2 |   |
|   | 3 | correct | 6.0 |   |
| 10 | 1 | false | 33.7 | 5.9 |
|   | 2 | correct | 2.6 |   |
|   | 3 | correct | 1.9 |   |
| 11 | 1 | correct | 2.4 | 5.8 |
|   | 2 | correct | 2.3 |   |
|   | 3 | correct | 1.8 |   |
| 12 | 1 | correct | 1.4 | 4.4 |
|   | 2 | correct | 1.9 |   |
|   | 3 | correct | 2.1 |   |

FIG. 11

| Insertion | Angle $B_0$ [°] | Slice | Detected | Error [mm] | Error [°] |
|---|---|---|---|---|---|
| 1 | 91.2 | 1 | correct | 1.0 | 2.8 |
|   |      | 2 | correct | 0.2 |     |
|   |      | 3 | correct | 0.4 |     |
| 2 | 99.6 | 1 | missed  | N/A | 5.3 |
|   |      | 2 | correct | 0.6 |     |
|   |      | 3 | correct | 0.7 |     |
| 3 | 56.2 | 1 | correct | 3.7 | 13.1 |
|   |      | 2 | correct | 2.8 |     |
|   |      | 3 | correct | 0.3 |     |
| 4 | 32.8 | 1 | correct | 0.52 | 19.0 |
|   |      | 2 | missed  | N/A |     |
|   |      | 3 | correct | 5.8 |     |
| 5 | 27.5 | 1 | missed  | N/A | N/A |
|   |      | 2 | missed  | N/A |     |
|   |      | 3 | missed  | N/A |     |
| 6 | 100.0 | 1 | correct | 0.8 | 16.1 |
|   |      | 2 | correct | 2.0 |     |
|   |      | 3 | correct | 3.1 |     |

| Timestep | Needle [mm] | Model [mm] | Iterations | Error [mm] | Error [°] |
|---|---|---|---|---|---|
| 1 | 0.0 | N/A | | | |
| 2 | 9.6 | N/A | | | |
| 3 | 13.1 | N/A | | | |
| 4 | 19.1 | N/A | | | |
| 5 | 24.5 | 17.4 | 17 | 1.4 | 0.7 |
| 6 | 25.2 | 23.1 | 33 | 2.5 | 1.8 |
| 7 | 30.3 | 32.9 | 24 | 0.7 | 2.3 |
| 8 | 36.4 | 37.7 | 24 | 1.1 | 2.2 |
| 9 | 39.9 | 42.7 | 32 | 1.5 | 2.9 |
| 10 | 44.1 | 46.5 | 19 | 2.3 | 3.3 |
| 11 | 54.6 | 55.6 | 26 | 2.3 | 1.6 |
| 12 | 60.7 | 62.2 | 27 | 2.0 | 1.2 |
| 13 | 65.2 | 67.0 | 25 | 1.9 | 1.3 |
| 14 | 66.8 | 69.6 | 25 | 2.5 | 1.8 |
| 15 | 69.4 | 72.5 | 20 | 3.8 | 2.4 |
| 16 | 73.5 | 74.3 | 23 | 5.9 | 0.5 |

SYSTEM AND METHOD FOR PASSIVE MEDICAL DEVICE NAVIGATION UNDER REAL-TIME MRI GUIDANCE

CROSS REFERENCE TO RELATED UNITED STATES APPLICATIONS

This application claims priority from "Passive Medical Device Navigation Under Real-Time MR Imaging", U.S. Provisional Application No. 61/352,854 of Strehl, et al., filed Jun. 9, 2010, the contents of which are herein incorporated by reference in their entirety.

TECHNICAL FIELD

This disclosure is directed to methods for passive needle guidance during MRI guided procedures, using only image intensity information.

DISCUSSION OF THE RELATED ART

Interventional procedures often require accurate placement of medical devices, e.g. to acquire a tissue sample with a biopsy needle or to place radioactive seeds for brachytherapy. Magnetic Resonance Imaging (MRI) provides excellent soft-tissue contrast and multiplanar imaging capabilities while not exposing the patient and physician to ionizing radiation. It is therefore an ideal modality for monitoring and guiding interventional procedures such as biopsies, drainages, and ablations. The primary motivations for performing these procedures under image guidance are needle visualization and navigation. Due to recent technological advances real-time Magnetic Resonance Imaging (MRI) became feasible and its usage grows for guiding interventional procedures, particularly those involving needle placements. For general adoption in clinical practice new tools and methods are required to make these procedures safe, effective and efficient. The successful outcome depends on precise navigation of the needle to a target location while avoiding damage to surrounding anatomical structures. To ensure optimal visualization for the physician it is desirable to utilize the multiplanar imaging capabilities of MRI and realign the imaging slices with respect to the current device position during the procedure. This can be accomplished by automated needle localization and has the potential to shorten the time required to perform interventional procedures and provide the physician with additional information. The known position of the needle makes it possible to dynamically align the imaging slices and clearly visualize the device as well as surrounding anatomy. Current techniques for automated needle tracking under MRI require additional hardware and/or modifications of the existing system and therefore increase the overall complexity of the procedure and cause additional costs.

Methods for medical device tracking under MRI can be divided into two basic strategies, namely active and passive techniques. The difference between those two techniques is the information that is used to localize the medical instrument. Active approaches calculate the device position independently of the acquired MR images by using additional sensors and hardware. Active techniques for instrument tracking can yield high accuracy at frame rates suitable for real-time localization but require additional dedicated hardware, modifications to the existing system, and calibration. In contrast, passive methods only use the signal intensities in the MR image to localize the medical device. However, compared to the active tracking techniques, there are only few reported approaches for passive device localization under MRI so far.

SUMMARY OF THE INVENTION

Exemplary embodiments of the invention as described herein generally include methods and systems for needle navigation under real-time MR image guidance that can be readily integrated into the standard process of an MR-guided interventional procedure for improving the workflow. A system according to an embodiment of the invention can be integrated into commercially available front ends. Before starting a procedure, a needle trajectory can be interactively defined using high resolution diagnostic MRI data. During the procedure, a detection module can register the initial needle position by identifying candidates for the needle artifact in real-time MR images and deciding for the most likely candidate. Continuous tracking of the needle position can be achieved by applying a 3-D parametric model-fitting approach, based on a regular cylinder needle model. The needle position can found by minimizing a cost function that weighs image intensities depending on their relative position to the needle artifact.

A detection module according to an embodiment of the invention combines the prior knowledge, an intelligent strategy for image acquisition, and an algorithm to detect the artifact of the needle as it is introduced along the proximity of the trajectory path, and provides an initial needle position to the image-based needle tracking in the third step. Needle tracking is accomplished using a 3-D model fitting approach based on the void signal caused by the needle and involves real-time imaging with dynamic slice control.

A detection module according to an embodiment of the invention was evaluated in a real-time MRI setting. Tracking is simulated using multiple 3-dimensional (3D) MRI datasets acquired during needle insertion in a pork sample. The results are promising with a detection rate of 87% and a mean accuracy better than 2.3 mm for the detection algorithm. Needle tracking was achieved with an average distance to the true needle tip of 2.3 mm and a mean 1.8 deviation for reconstructing the needle direction.

According to an aspect of the invention, there is provided a method for tracking a needle along a path under real-time magnetic resonance imaging (MRI) guidance, including extracting a candidate needle artifact region from a plurality of incoming MR images of a needle inside biological tissue, determining an initial needle direction vector from the candidate needle artifact region in each of the plurality of incoming needle images, determining an initial needle base point from an intersection of the needle direction vector with a first incoming needle image, and an initial needle tip point from an intersection of the needle direction vector with a last incoming needle image, and tracking the needle by minimizing a cost function of the initial base point and initial direction vector to calculate an updated base point and updated direction vector, where the updated base point and direction vector are used to visualize the advance of the needle along the path through the biological tissue.

According to a further aspect of the invention, extracting candidate needle artifact regions includes receiving a current MR needle image defined as an MR image containing the needle artifact, extracting a plurality of pixel regions from the current MR needle image having a lower image intensity than surrounding pixels, calculating a plurality of features for each pixel region, and selecting one or more pixel regions, based on the features of each region, that are likely to represent a needle artifact, as candidate needle artifact regions, where, if more than one pixel region is selected, choosing a region closest to the path as the candidate needle artifact region.

According to a further aspect of the invention, the plurality of pixel regions are extracted from the current MR needle image by subtracting the current MR needle image from a background model, extracting those pixels whose intensity difference with respect to corresponding pixels in the background model is greater than a predetermined threshold, and using connected-component analysis to form pixel regions from the extracted pixels.

According to a further aspect of the invention, a pixel i is extracted if the intensity difference $E_t(x_i)-I_t(x_i) \geq d_{threshold}$, where $E_t$ is the background model, $I_t$ is the current image, and $x_i$ is the position of pixel i.

According to a further aspect of the invention, the method includes, if no region is selected as a candidate needle artifact region, updating the background model with the current image.

According to a further aspect of the invention, features calculated for the extracted pixel regions include an area, a perimeter, a circularity, a centroid, and a distance from the centroid to the planned path, where regions whose centroid is less than a predetermined distance from the planned path, whose circularity is less than a predetermined maximum, and whose area is within a predetermined range, are selected as candidate needle artifact regions.

According to a further aspect of the invention, the cost function of the base point and direction vector is given by $$J(b, d) = \sum_{i=0}^{N} I_i w_k(k(x_i, b, d)) w_l(l(x_i, b, d)) \in R,$$

where base point $b=(b_x, b_y, b_z)^T \in R^3$, direction vector $d=(d_x, d_y, d_z)^T \in R^3$, $x_i$ is the position of pixel i, $I_i$ is the image intensity for pixel i, N is the number of pixels, $w_k$ is given by $w_k(k(x,b,d))=H(k(x,b,d))H(1-k(x,b,d))$, where H is the Heaviside step function and k is given by $$k(x, b, d) = \frac{(x-b)^T d}{\|d\|^2} \in R,$$

$w_l$ is given by $$w_l(l(x, b, d)) = N(l(x, b, d), \mu_1, \sigma_1) - \frac{1}{2} N(l(x, b, d), \mu_2, \sigma_2),$$

where l is given by $$l(x, b, d) = \frac{1}{r} \|p(x, b, d) - x\| \in R,$$

$p(x,b,d)=b+k(x,b,d)d \in R^3$, and $N(x, \mu, \sigma)$ denotes the probability density function for a univariate normal distribution with the mean $\mu$ and standard deviation $\sigma$.

According to a further aspect of the invention, minimizing the cost function comprises acquiring at least three images with respect to a current needle position, where at least two images are parallel to the needle and perpendicular to each other, and the third image is perpendicular to longitudinal axis of the needle, and minimizing the cost function in the images to obtain a new needle position.

According to a further aspect of the invention, minimizing the cost function comprises updating a parameter vector p=(b, d) according to $$p_{i+1} = \underset{p \in N_i}{\mathrm{argmin}} J(p)$$

where $N_i$ is a neighborhood about p generated for each iteration i by varying the vector p by a stepsize$\pm\gamma_{BN}$ in each dimension.

According to a further aspect of the invention, minimizing the cost function comprises updating a parameter vector p=(b, d) according to $p_{i+1}=p_i-\gamma_{GD}\nabla J(p_i)$, where $\gamma_{GD}$ denotes a step size.

According to another aspect of the invention, there is provided a program storage device readable by a computer, tangibly embodying a program of instructions executable by the computer to perform the method steps for tracking a needle along a path under real-time magnetic resonance imaging (MRI) guidance.

BRIEF DESCRIPTION OF THE DRAWINGS

FIGS. 1(a)-(b) depict MR images showing a needle artifact, according to an embodiment of the invention.

FIG. 3 3.5 depicts section of a needle artifact in an with a 3-D FLASH sequence, according to an embodiment of the invention.

FIG. 4 3.6 shows a longitudinal section of a needle artifact in MR images acquired with a 3-D FLASH sequence, according to an embodiment of the invention.

FIGS. 3(a)-(b) shows a planned path in a 3-D view and the layout of the three image slices during real-time imaging, according to an embodiment of the invention.

FIG. 4 illustrates directions of the Freeman chaincode, according to an embodiment of the invention.

FIGS. 5(a)-(b) illustrates contour extraction and perimeter estimation for artificially generated regions in a binary image, according to an embodiment of the invention.

FIG. 11 is a table of detailed results for the distance accuracy test of needle detection, according to an embodiment of the invention.

DETAILED DESCRIPTION OF EXEMPLARY EMBODIMENTS

Figure 1:
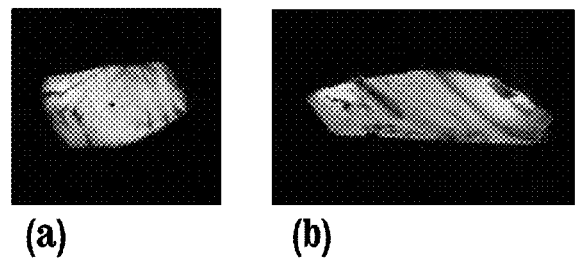
FIG. 1 3.2: is a block diagram MR scanner network for real-time acquisition using the IFE, according to an embodiment of the invention.

Exemplary embodiments of the invention as described herein generally include systems and methods for passive needle guidance during MRI guided procedures using only image intensity information. Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

As used herein, the term "image" refers to multi-dimensional data composed of discrete image elements (e.g., pixels for 2-dimensional images and voxels for 3-dimensional images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R or $R^7$, the methods of the inventions are not limited to such images, and can be applied to images of any dimension, e.g., a 2-dimensional picture or a 3-dimensional volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

MRI Basics

MRI possesses several unique characteristics that differentiate it from other imaging modalities. The underlying physics and design of MRI enables image acquisition as 2-D slices oriented in any arbitrary position or as 3-D volumes. This is contrary to other imaging modalities such as CT whose image acquisition is dependent on the orientation of the detection hardware with respect to the patient or object. Unlike CT, X-ray, positron emission tomography (PET), and single photon emission tomography (SPECT), MRI does not require exposure of the patient and/or the physician/technical staff to ionizing radiation during the scan. Another feature of MRI is its ability to acquire images with high soft tissue contrast which is valuable for neurological, intravascular, musculoskeletal, and oncological imaging where clear depiction of abnormal tissue is crucial. Some lesions, e.g. in the liver or breast, are not visible with other imaging modalities making MRI indispensable for diagnosis and treatment.

Interventional Radiology (IR) is a subfield of radiology, where minimally invasive procedures are performed under image guidance. Compared to open surgery, minimally invasive procedures cause less patient trauma and generally require shorter recovery times. Consequently, these procedures can often be performed in an outpatient setting resulting in reduced overall procedure cost. There is growing interest in using MRI for IR procedures primarily because of the reasons outlined above. However, besides scanner availability and cost, the use of MRI for interventional procedures has other hurdles to overcome, including limited access to patients within the scanner, long image acquisition times, and the need for special MR-compatible instruments, all of which have hindered the adoption of MRI in interventional radiology.

MRI has traditionally been a purely diagnostic imaging modality with a corresponding static workflow for a conventional MR exam. Imaging is performed by selecting a particular pulse sequence, fixing the imaging parameters and prescribing specific image slice locations. The image acquisition for each pulse sequence is therefore defined explicitly by the fixed imaging parameters. For IR procedures, real-time imaging with real-time manipulation of slice positions is needed. Conventional product functionality for real-time imaging is limited to single slice acquisition with limited modification of imaging parameters during imaging. Furthermore, visualization capabilities are restrictive.

Needle Artifacts Under MRI

Most medical devices used for interventions are made out of metal and generate artifacts in MR images. The magnetization of the needle generates a local signal drop in the MR images, referred to as a susceptibility artifact. This artifact is due to a magnetic susceptibility mismatch between the metallic needle and its surrounding tissue. Magnetic susceptibility is the degree of magnetization incurred by a material in response to an applied magnetic field. The susceptibility mismatch causes the needle to induce a local field inhomogeneity, in turn disturbing the coherent MR signal and producing a loss of signal or signal void. The susceptibility artifact often appears significantly larger than the physical size of the needle. The size of the artifact has been shown to be dependent on the pulse sequence used, the material and shape of the metallic object, the magnetic field strength, and the orientation of the object with respect to the main magnetic field.

To detect and track the needle artifact, it is beneficial to accurately predict the appearance of the needle artifact. However, this is challenging, because the size and shape of the artifact are dependent on so many factors. Experiments have found that the needle artifact can be described as a cylindrical signal void as shown in FIG. 1. For images acquired perpendicular to the needle axis, the artifact cross section appeared circular, as shown in FIG. 1(a). For slices acquired parallel to the needle axis, the artifact generated an elongated signal void along the centerline of the needle, as shown in FIG. 1(b). These MR images clearly depict the symmetry of the needle artifact and the size of the generated artifact.

The orientation of the needle with respect to the main magnetic field direction $B_0$ significantly influences the size of the needle artifact. In a MR scanner with a cylindrical bore, $B_0$ is parallel to the scanner table. The magnetic field disturbance and thus the size of the artifact is maximal if the needle axis is perpendicular to $B_0$ and decreases rapidly for smaller angles. Furthermore, the shape of the needle artifact changes for needle directions approximately parallel to $B_0$ with a bell-like contour observed at the needle tip.

Overview

MR-guided interventions can be divided into two steps, namely a preoperative step and an intraoperative step. Before the procedure, in the preoperative step, diagnostic images are acquired to localize the lesion and plan a needle trajectory. During the intervention, in the intraoperative step, real-time imaging is used to monitor the position of the instrument and navigate it to the target location. To support these steps, a planning tool can be used to visualize a 3-D high resolution dataset and define the needle trajectory and a tracking tool can be used for needle localization using real-time images acquired during the intervention.

Once a trajectory is defined, a computer system can be used to control the scanner, run the needle tracking tool, and to visualize the acquired images. A needle tracking tool according to an embodiment of the invention includes two modules. A needle detection module can identify cross-sections of the needle artifact during insertion at the beginning of the procedure. Based on the position of the needle artifact in the MR images, the initial needle position can be reconstructed and used to initialize the tracking module. A needle tracking module uses a model-fitting approach based on a parametric cylinder model of the needle artifact.

According to an embodiment of the invention, the following assumptions were made in the development of the needle detection and tracking modules. First, it is assumed that no respiratory or cardiac motion is present and that the patient position does not change between the acquisition of the planning dataset and the intervention. This means the coordinate system is the same for planning and real-time imaging. Second, the needle is assumed to be rigid, i.e. does not bend during the insertion. Although this is the case during most procedures, there can be interventions where the needle is flexed on purpose, for example to steer the needle tip in a certain direction that is not reachable with a straight trajectory.

Figure 2:
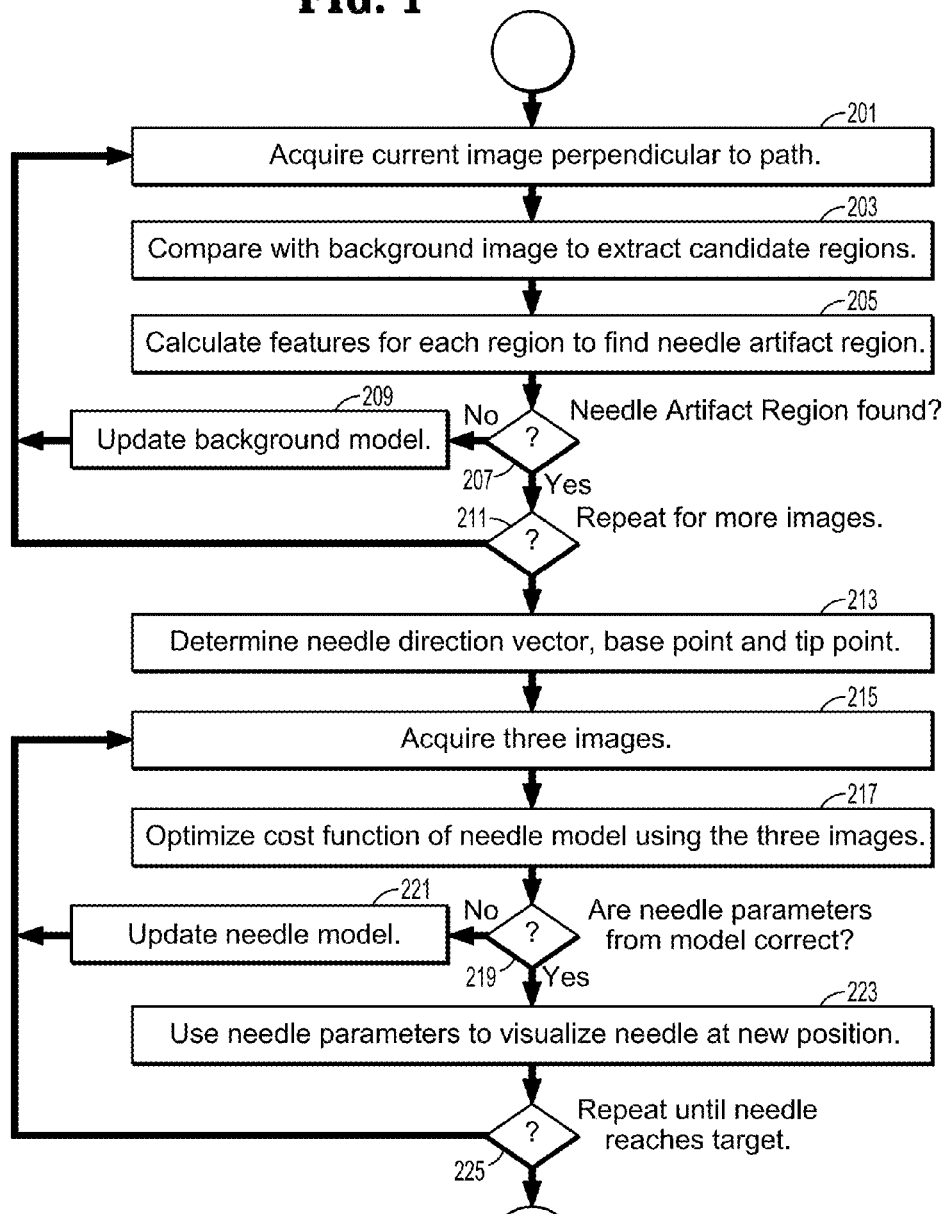
FIG. 2 is a flowchart of an algorithm for detecting a needle and tracking the needle along a planned path, according to an embodiment of the invention.

FIG. 2 is a flowchart of an algorithm for detecting a needle and tracking the needle along a planned path, according to an embodiment of the invention. Referring now to the figure, a needle detection and tracking algorithm begins at step 201 by acquiring a current image perpendicular to the planned needle path of the needle inserted into biological tissue, such as a patient. Although for simplicity the foregoing description is in terms of scalar valued 2D images, methods according to other embodiments of the invention are applicable to scalar valued images of 3- or more dimensions. This current image is compared with a background model at step 203 to extract regions of pixels whose intensity is lower than the surrounding pixels. A plurality of features are calculated for the extracted pixel regions at step 205, and based on these features, one region is sought as a candidate needle artifact region. If, at step 207, a region is found, steps 201, 203, and 205 are repeated from step 211 to provide a plurality of images having a candidate needle artifact region. If no candidate needle artifact region is found in the current image, the background model is updated with the current image at step 209, and steps 201, 203, and 205 are repeated. After a needle artifact has been identified in at least two images, at step 213, an initial needle direction vector can be determined from an artifact centroid in at least two images, an initial needle base point is determined from an intersection of the needle direction vector with a first acquired image, and an initial needle tip point s determined from an intersection of the needle direction vector with a second acquired image. Alternatively, the initial needle base and tip points can be determined from the artifact centroids in the respective first and last images, and the initial needle direction can be determined from the initial needle base and tip points. Next, at step 215, at least three images are acquired, of which two are parallel to the planned path and perpendicular to each other, and the third is perpendicular to the planned path. The needle direction vector and base point are used to initialize a needle model, and a cost function of the needle model is optimized in the acquired images at step 217 to obtain new values for the needle base pint and direction vector. If, at step 219, these new values are not sufficiently close to the planned path, the needle model can be modified at step 221. Otherwise, these new values are used to update and realign the images of the needle as it is inserted further into the biological tissue, at step 223. Steps 215, 217, and 219 are repeated from step 225 until the needle reaches its target. These steps will be described in greater detail below.

Needle Detection

A needle detection module according to an embodiment of the invention can recognize the artifact of the needle during insertion. MR images are acquired during needle insertion using a real-time imaging sequence with the scan planes automatically aligned perpendicular to the planned trajectory. By detecting the needle artifact cross-section in at least two image slices, the position and orientation of the needle can be reconstructed.

Figure 3:
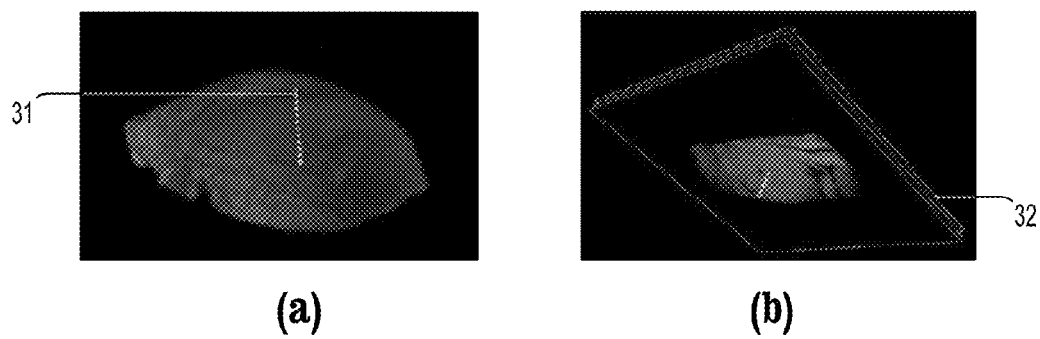

FIG. 3(a) depicts a planned path 31 in the 3-D view, and FIG. 3(b) depicts the layout of three image slices 32 during real-time imaging. For detection, the slices are aligned perpendicular to the planned trajectory with a predetermined default spacing to detect the circular cross-section of the needle artifact. An exemplary, non-limiting spacing is 7 mm.

The needle detection process includes three steps and is performed independently for each of a plurality of image slices. In an exemplary, non-limiting embodiment, three image slices are used. First, an incoming image is compared to a background model to identify regions showing a drop in image intensity which may therefore contain the needle artifact. Next, features are computed for those candidate regions, e.g., the area, circularity, and distance to the planned path. Finally, these features are used to filter the candidate regions, discarding those that are not matching the expected shape of the needle artifact or are further away from the planned trajectory than a user-defined maximum distance. In the case of more than one remaining candidate, the one closer to the planned trajectory is chosen. These steps are described in greater detail below.

There are inherent tradeoffs between spatial resolution, temporal resolution and signal in MRI. For adequate visualization of the needle cross-section or diameter, a sufficient spatial resolution should be maintained. For example, if the needle artifact appears with a diameter of 6 mm, an in-plane spatial resolution of 1.5 mm would depict the needle diameter with 4 pixels. A tracking algorithm according to an embodiment of the invention benefits from a higher spatial resolution as it would result in a less sparse 3-D data set for model fitting and would likely yield a more robust optimization with better convergence. Therefore, a careful consideration of imaging parameters can achieve a sufficient spatial resolution to resolve the needle artifact while providing an acceptable temporal resolution for tracking the needle during insertion and a sufficient signal for depicting the target anatomy.

Background Subtraction

Background subtraction is used in computer vision to identify moving objects in images acquired with a static camera. For detecting a needle artifact, the background is defined to be the anatomical structure in the MR image at a specific location.

A background subtraction model for needle detection according to an embodiment of the invention is based on an exponential moving average (EMA). The EMA has the same size as the acquired MR image and is used to approximate the average intensity independently for every pixel location $(u, v) \in R^2$. With the first image $I_0$ acquired perpendicular to the planned path, the EMA $E_0$ is initialized and updated iteratively for every image $I_t$ at time step t according to $$E_{t+1}(u,v) = (1-\alpha)E_t(u,v) + \alpha I_t(u,v). \quad (1)$$

The factor $\alpha \in [0,1]$ is called the learning rate and determines the weighting of $I_t$ relative to the current $E_t$. Thus, the contribution of previous images to E decreases exponentially.

To extract the pixels in the incoming image frame that exhibit a significantly lower image intensity as compared to the background model, a binary difference image $D_t$ may be defined as $$D_t(u, v) = \begin{cases} 1, & \text{if } E_t(u, v) - I_t(u, v) \geq d_{thresh}, \\ 0, & \text{otherwise.} \end{cases} \quad (2)$$

Exemplary, non-limiting values of threshold $d_{thresh}$ and $\alpha$ were heuristically set to 50 and 0.25, respectively.

Feature Extraction and Filtering

In a next step according to an embodiment of the invention, connected component labeling is used to extract regions in the binary difference image D, and several features are calculated for each region. Depending on these features, a region is either classified as a needle artifact cross-section or discarded.

An algorithm according to an embodiment of the invention for connected component labeling processes the image in a row-wise fashion, requiring two passes over the entire image and identifies 4-connected regions, i.e. a pixel is assigned to a region if it has at least one pixel in its direct vertical or horizontal neighborhood that is part of the region. The output is an image containing a region label number for each pixel. In addition, the bounding box for each extracted region is calculated and used for the following computations.

Based on the labeled image, several features are calculated for each region. The area and circularity are used to discard regions that do not match with the expected circular shape of the needle artifact cross-section. Furthermore, to filter candidate regions that are unlikely to represent the needle artifact, the distance of the centroid to the planned path is calculated.

The area A of a region R is obtained by summation over all pixels it includes as described by $$A = \sum_{(u,v) \in R} 1, \quad (3)$$

and the region's centroid $c = (\bar{u}, \bar{v})^T \in R^2$ is computed as the arithmetic mean of the pixel coordinates according to $$\bar{u} = \frac{1}{A} \sum_{(u,v) \in R} u, \quad (4)$$

$$\bar{v} = \frac{1}{A} \sum_{(u,v) \in R} v. \quad (5)$$

To calculate the distance L of a region's centroid c to the planned trajectory, defined by an entry point $e \in R^3$ and a target point $t \in R^3$, c first has to be projected onto the planned trajectory. The projection $p \in R^3$ can be calculated as $$p = e + \frac{(e - \phi(c))^T (t - e)}{\|t - e\|^2} (t - e), \quad (6)$$

where $\| \|$ denotes the Euclidean distance and $\phi$ is the transformation from the image to the scanner coordinate system. Consequently, L reads as $$L = \|p - \phi(c)\|.$$

Figure 4:
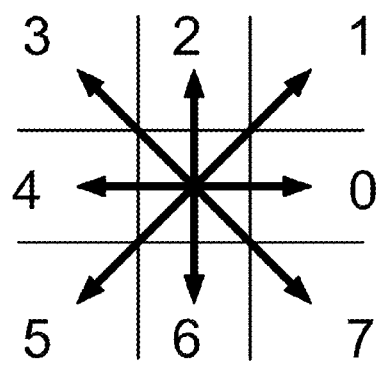

Various techniques can be used to estimate the perimeter of a shape in a digital image. According to an embodiment of the invention, a Freeman chaincode algorithm, illustrated in FIG. 4, can be used. Here, the 8-connected boundary pixels of a region are extracted and an arbitrary pixel of this contour is chosen as the starting point. From the starting point, the entire contour is traversed and every transition from a pixel to its neighbor is encoded with the corresponding chaincode direction. Based on the chaincode representation of the contour, the perimeter P of a region can then be estimated as $$P = n_e + \sqrt{2} n_o, \quad (8)$$

where $n_o$ is the number of odd and $n_e$ is the number of even chaincodes. This estimation is derived from the distance between neighboring pixel centers being 1 for vertical or horizontal steps and $\sqrt{2}$ for diagonal steps.

Using the perimeter, it is also possible to estimate the circularity of a region. Circularity C is a dimensionless quantity that can characterize the compactness of a shape. One way according to an embodiment of the invention to estimate C is by comparing the area of a region to the area enclosed by a circle with equal perimeter as described by $$C = \frac{P^2}{4\pi A}. \quad (9)$$

Figures 5, 6:
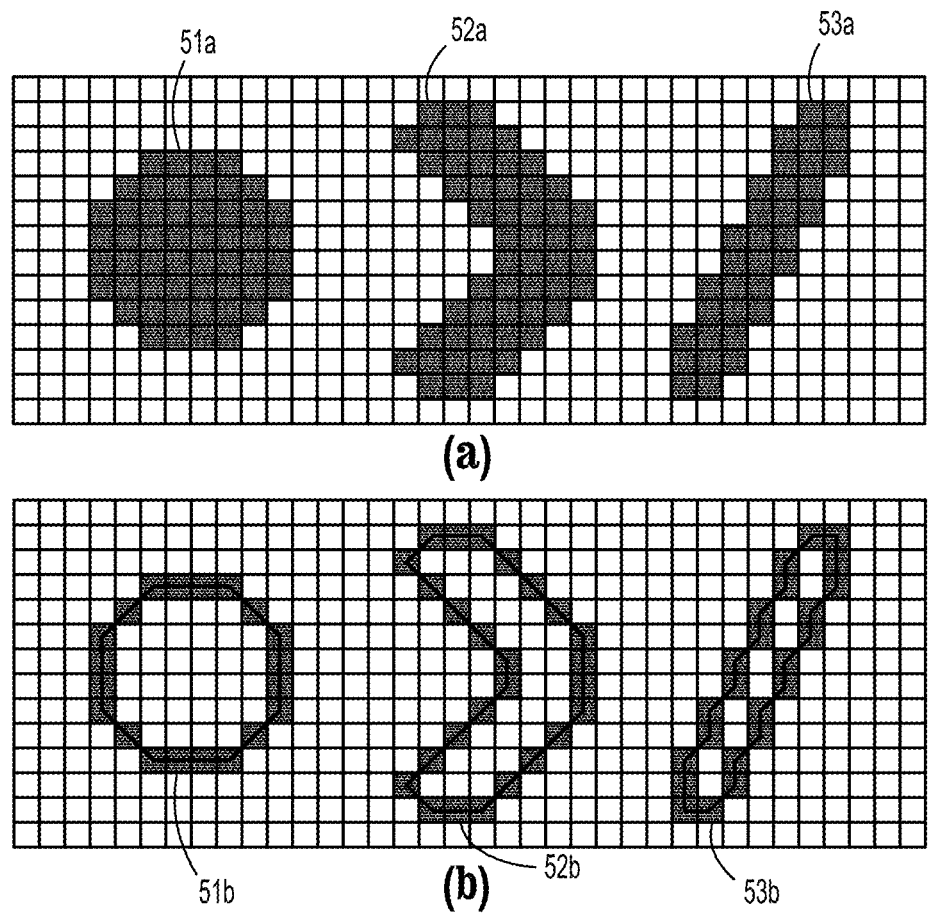
FIG. 6 is a table showing area, perimeter, and circularity for the regions shown in FIGS. 5(a)-(b), according to an embodiment of the invention.

This definition results in a minimal circularity value of 1 for a circle and larger values for less compact, e.g. elongated shapes, but only holds true for shape measurements in a continuous space. In the discrete case of binary images, square and circular shapes have minimal circularity values smaller than 1, due to discretization and the fact that the perimeter tends to be under-estimated when using the chaincode approach. However, this estimation is sufficient for characterizing the compactness of regions in digital images for the purpose of comparing different shapes. FIGS. 5(a)-(b) show the extraction of boundary pixels and the approximated perimeter for three artificially generated regions in a binary image. FIG. 85(a) depicts a raw binary image showing the three different regions 51a, 52a, and 53a, while FIG. 5(b) depicts the extracted 8-connected contours and perimeters 51b, 52b, and 53b. The regions are, from left to right, (1) a circular region 51a, (2) an arrowhead-like region 52a, and (3)

an elongated region 53a. The table in FIG. 6 contains the area, perimeter, and circularity calculation results for these three examples.

Experiments using different filter settings to filter the candidate regions have shown that a maximum circularity C of 1.5 is suitable for discarding intensity changes caused by motion or noise. Although embodiments of the invention assume no respiratory and cardiac motion, needle insertion can cause a displacement of tissue, often resulting in elongated regions showing a signal drop.

According to an embodiment of the invention, a window filter was applied to the expected area of the needle artifact cross section, discarding regions that are either too small or too large. Those candidates satisfying $$\lfloor 0.75\pi r^2 \rfloor \leq A \leq \lceil 1.25\pi r^2 \rceil \qquad (10)$$

may be retained, where r is the approximate needle artifact radius. Experiments of an embodiment of the invention showed that the coefficients 0.75 for the lower and 1.25 for the upper bound generate a suitable window size.

Another aspect that first showed up as a system according to an embodiment of the invention was tested on a MR scanner is that a physician's hand as well as its corresponding motion can appear in the acquired images, generating undesirable changes in the image signal intensity. To minimize the effect of these undesirable signal changes, a region of interest is defined around the planned trajectory and used to discard candidates based on their distance L from the trajectory. This maximum distance can be set by a user. Exemplary, non-limiting values of the maximum distance are about 30-40 mm.

Needle Tracking

Most common object recognition and tracking approaches employed in computer vision are based on identifying local features of an object in a projection image, e.g. a photograph or video frame. These features are used as descriptors to characterize the visual appearance of the object and may include information about edges, texture, or color distribution. Tracking can then be accomplished by retrieving the same features in subsequent observations and matching them with their initial position.

However, the needle artifact in an MR image does not exhibit any explicit features or characteristic keypoints suitable for tracking. It is merely defined by the surrounding tissue. If the neighboring tissue shows high image intensities, the artifact has well defined boundaries, whereas in image regions with lower signal values, it may blur with the background. Therefore, to localize a needle only using the intensity and spatial information of the MR image slices, a suitable approach must be developed based on the appearance of the needle artifact as a cylindrical signal drop.

Another factor is the nature of the available information, namely in the form of 2-D image slices. Most 3-D pose estimation applications in the medical field employ either 3-D datasets, e.g. such as CT volumes, or multiple 2-D images that are acquired using a projective geometry, such as fluoroscopy. According to an embodiment of the invention, the 3-D position of the needle is estimated from the MR image slices and two general strategies are applicable:

1. Processing the images separately and combining the results to estimate the 3-D pose; or
2. Combining the image slices into a sparse 3-D dataset.

The first approach leads to a 'Bottom Up' technique, which uses standard image processing algorithms, to identify cross or longitudinal sections in the single images, and merges the observations to obtain an estimate for the 3-D position. However, these techniques require assumptions about the relative position of the needle with respect to the imaging plane.

In contrast, the second approach leads to a 'Top Down' technique, in which the single images are combined into a sparse volume dataset, and the position of the needle is estimated, e.g. by fitting a 3-D model. Top down approaches require no assumptions concerning the relative position of the needle with respect to the image slices. Images acquired with arbitrary orientations can be utilized, but of course various acquisition strategies yield different information content.

According to an embodiment of the invention, a parametric rigid cylinder is used to model the needle artifact and a cost function is derived by weighting the image intensities depending on their position relative to the needle artifact. Based on an initialization, the needle position is estimated by finding the best fit of the model to the available images. This results in a non-linear optimization task, and according to embodiments of the invention, either a best neighbor or a gradient descent algorithm can be applied to iteratively update the needle position until the cost function yields a local minimum. Tracking is accomplished by continuously repeating this model-fitting algorithm for newly acquired MR images.

Needle Model

According to an embodiment of the invention, the needle artifact is modeled as a regular cylinder, assuming a rigid needle. The model is parameterized in a scanner coordinate system by a base point $b=(b_x, b_y, b_z)^T \in R^3$, a direction vector $d=(d_x, d_y, d_z)^T \in R^3$, and radius r. As d is not normalized it encodes both the direction and the length of the needle artifact $\|d\|$.

Due to the symmetry of this parameterization, the relative position of a pixel $x=(x, y, z)^T \in R^3$ to the needle artifact can be described by the orthogonal projection $$p(x, b, d) = b + k(x, b, d)d \in R^3, \qquad (11)$$

where $$k(x, b, d) = \frac{(x-b)^T d}{\|d\|^2} \in R \qquad (12)$$

describes the position of the projection of x onto the line segment from b to the needle tip b+d, with the following meanings:

$k(x,b,d)<0$: projection of x is on the backward extension of the line segment;

$k(x,b,d)=0$: projection of x is b;

$0<k(x,b,d)<1$: projection of x is interior to the line segment;

$k(x,b,d)=1$: projection of x is b+d;

$k(x,b,d)>1$: projection of x is on the forward extension of the line segment. (13)

The Euclidean distance l(x,b,d) of x from the needle centerline, scaled by the radius r, can be calculated from $$l(x, b, d) = \frac{1}{r}\|p(x, b, d) - x\| \in R. \qquad (14)$$

Two cases can be differentiated:

$l(x,b,d) \leq 1$: x lies inside the cylinder of radius r;

$l(x,b,d) > 1$: x lies outside the cylinder of radius r. (15)

Cost Function

A cost function J according to an embodiment of the invention for determining the needle artifact parameters b and d and for optimally resolving the true needle position weighs the image intensity $I_i$ of each pixel $x_i$ by its relative position to the needle artifact $k(x,b,d)$ using EQS. (13) and the Euclidean distance to the needle centerline $l(x,b,d)$ using EQS. (15). J is minimal for the needle position and is given by $$J(b, d) = \sum_{i=0}^{N} I_i w_k(k(x_i, b, d)) w_l(l(x_i, b, d)) \in R, \quad (16)$$

where N denotes the number of pixels $x_i$ in the image slices. The term $w_k(k(x, b, d))$, including the relative position of x to the cost function, is given by $$w_k(k(x,b,d)) = H(k(x,b,d))H(1-k(x,b,d)), \quad (17)$$

where H is the Heaviside function, defined by $$H(x) = \begin{cases} 0, & \text{if } x \leq 0, \\ 1, & \text{otherwise.} \end{cases} \quad (18)$$

Thus $w_k(k(x, b, d))$ results in a value of 1 only for the pixel locations whose projection are interior to the line segment defined by b and d.

The term $w_l$ in the cost function weights image intensities, depending on their distance to the centerline given by $l(x, b, d)$. According to embodiments of the invention, different functions can be used for this task and effect the resulting shape of the cost function. For example, to weigh all pixels inside the cylinder uniformly, the Heaviside function can be used, thus resulting in the term $H(1-l(x, b, d))$. The resulting cost function exhibits a low value at a position of the needle model, where low image intensities occur in a cylindrical shape, but this weighting also yields a minimum for two degenerate cases. First, the needle length correlates with the number of contributing image intensities, thus decreasing the overall cost for a decreasing needle length. Second, because of the sparsity of image information, the cost function exhibits a minimum for needle positions that lie outside of the MR image planes due to the fact that, no intensity information is available for these locations.

According to an embodiment of the invention, to resolve these issues, a weighting function is formulated to take into account the intensity difference of the needle artifact and its neighborhood. This can be achieved by assigning a positive weighting factor to pixels with low intensities inside the artifact and a negative weighting factor for pixels with higher intensities in the surrounding tissue. Furthermore, the weighting function should converge to zero for high values of $l(x, b, d)$ to discard intensities that do not contribute to the appearance of the needle artifact due to a large distance from the needle centerline. A suitable weighting function is based on the difference of two normal distributions and can be described by $$w_l(l(x, b, d)) = N(l(x, b, d), \mu_1, \sigma_1) - \frac{1}{2} N(l(x, b, d), \mu_2, \sigma_2), \quad (19)$$

where $N(x, \mu, \sigma)$ denotes the probability density function for a univariate normal distribution with the mean $\mu$ and standard deviation $\sigma$.

Figure 7:
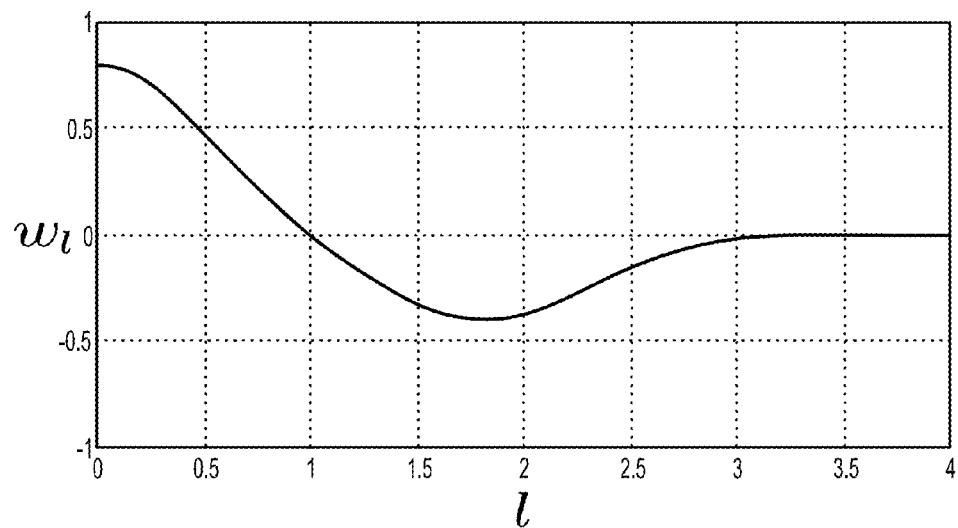
FIG. 7 is a plot of the weighting function, given in EQ. (19), according to an embodiment of the invention.
Figure 8:
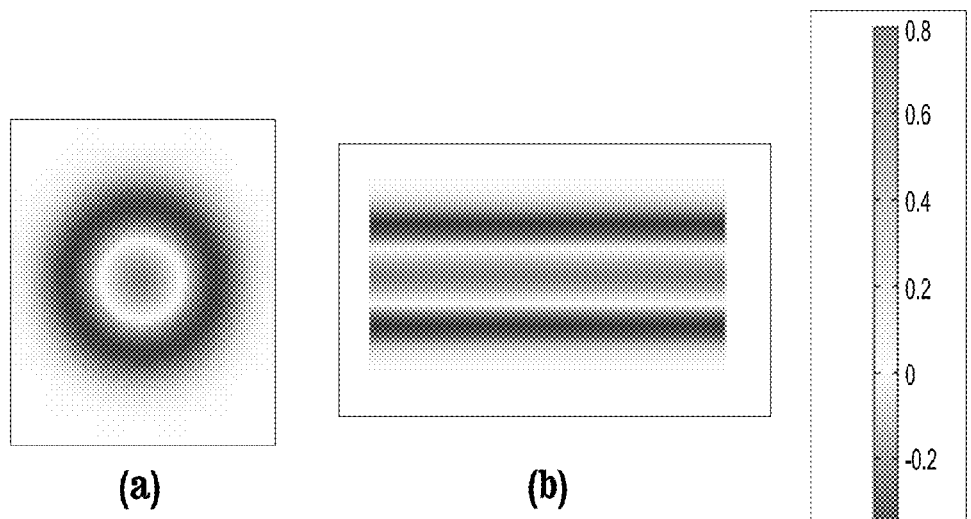
FIGS. 8(a)-(b) illustrates the weighting of image intensities with both $w_k$ and $w_l$ applied, according to EQ. (16) for an image acquired perpendicular to a needle artifact and an image acquired along a needle artifact centerline, according to an embodiment of the invention.

According to an embodiment of the invention, $\mu_1=0$ and $\sigma_1=\sigma_2=0.50$ were fixed, and $\mu_2 \approx 1.808$ was calculated so that the weighting function yields a maximum for intensities close to the needle centerline, a zero crossing for $l(x, b, d)=1$, and a minimum for intensities located outside of the cylindrical needle artifact. FIG. 7 depicts a plot of the weighting function $w_l$ as a function of l, given in EQ. (19), used to weight pixels depending on their distance from the needle artifact centerline given by l. FIGS. 8(a)-(b) depicts the weighting of image intensities with both $w_k$ and $w_l$ applied, according to EQ. (16) for an image acquired perpendicular to the needle artifact in FIG. 8(a) and an image acquired along the needle artifact centerline in FIG. 8(b).

Optimization

Estimation of the needle artifact position can be accomplished by minimizing the cost function given in EQ. (16) with respect to the parameters b and d. According to embodiments of the invention, two iterative algorithms are implemented for this non-linear optimization task, namely a best neighbor and a gradient descent optimizer. For ease of notation, the parameters of the needle model are combined in $p=(b, d) \in R^6$ for the following sections.

Best Neighbor Optimization

The best neighbor optimizer is a simple, local optimization algorithm that does not require the calculation of derivatives. It is based on a sub-sampling of the cost function on an equidistant grid, the so called neighborhood in the parameter space. For an n-dimensional parameter vector $p \in R^n$, the neighborhood has 2n vectors, generated by varying the parameter vector by $\pm \gamma_{BN}$ in each dimension. $\gamma_{BN}$ determines the step size used to generate the neighborhood N and is initialized at the beginning of the optimization.

The cost function J is optimized by iteratively updating the parameter vector p according to $$p_{i+1} = \underset{p \in N_i}{\operatorname{argmin}} J(p) \quad (20)$$

Thus, for each iteration, 12 evaluations of the cost function for the 6-dimensional parameterization of the needle artifact position are required. If no parameter vector in the neighborhood of $p_i$ yields a lower cost, the step size $\gamma_{BN}$ is halved and $p_i$ is retained, i.e. $p_{i+1}=p_i$. This results in a finer local sampling in the next iteration and indicates a local minimum in the proximity of the current parameter vector. The algorithm terminates when the step size drops below a user-defined minimum. Exemplary, non-limiting of the initial and minimum step size are 4 mm and 0.1 mm, respectively.

Gradient Descent Optimization

The gradient descent optimizer is a first-order local optimization algorithm and therefore requires the partial derivatives of the cost function J with respect to the parameter vector p. It is based on the fact that the gradient of a function gives the direction of steepest ascent and therefore taking a step in the opposite, i.e. negative direction of the gradient results in the steepest descent. For the purpose of minimization, the parameter vector is therefore updated according to $$p_{i+1} = p_i - \gamma_{GD} \nabla J(p_i), \quad (21)$$

where $\gamma_{GD}$ denotes the step size. The optimal choice of $\gamma_{GD}$ requires an additional 1-dimensional optimization for every iteration, often called a line search. According to an embodiment of the invention, a simple heuristic was used for needle localization. The step size is set to $\gamma_{GD}=1$ and the initial gradient is likewise scaled to a length of 1. If $p_{i+1}$ yields a lower cost, $\gamma_{GD}$ is doubled and the cost function is evaluated again until either a maximum step size is reached or the cost does not decrease any further. On the other hand, if $p_{i+1}$ does not yield a lower cost, $\gamma_{GD}$ is halved until either a lower cost is reached or the step size drops below a minimum and the optimization is terminated. Exemplary, non-limiting values for the maximum and minimum step size $\gamma_{GD}$ are 4 mm and 0.1 mm, respectively.

To use a gradient descent algorithm, the partial derivatives of J with respect to p have to be calculated. As J is a sum over all image pixels, the gradient is the sum of all individual gradients described by $$\frac{\partial J(p)}{\partial p} = \sum_{i=0}^{N} I_i \frac{\partial}{\partial p} w_k(k(x_i, b, d)) w_l(l(x_i, b, d)), \quad (22)$$

which expands to $$\frac{\partial J(p)}{\partial p} = \sum I_i \begin{pmatrix} H(1 - k(x_i, b, d)) w(l(x_i, b, d)) \frac{\partial}{\partial p} H(k(x_i, b, d)) + \\ H(k(x_i, b, d)) w(l(x_i, b, d)) \frac{\partial}{\partial p} H(1 - k(x_i, b, d)) + \\ H(k(x_i, b, d)) H(1 - k(x_i, b, d)) \frac{\partial}{\partial p} w(l(x_i, b, d)) \end{pmatrix}. \quad (23)$$

In this form the partial derivatives regarding b and d can be calculated by repeatedly applying the chain rule and inserting the derivatives of k(x, b, d) and l(x, b, d):

$$\frac{\partial k(x, b, d)}{\partial b} = \frac{-1}{d^T d} d, \quad (24)$$

$$\frac{\partial k(x, b, d)}{\partial d} = \frac{1}{d^T d}(x - b - 2k(x, b, d)d),$$

$$\frac{\partial l(x, b, d)}{\partial b} = \frac{1}{r\|b + k(x, b, d)d - x\|}(b + k(x, b, d)d = x),$$

$$\frac{\partial l(x, b, d)}{\partial d} = k(x, b, d)\frac{\partial k(x, b, d)}{\partial d}.$$

As the analytical derivative of the Heaviside function is by definition the Dirac delta function, the derivative has to be approximated. An exemplary, non-limiting approximation is the normal distribution N(x, 0, 0.1).

Experimental Evaluation

Experiments were performed to evaluate needle guidance systems according to embodiments of the invention. All experiments were conducted on a Siemens Magnetom Espree 1.5T MR scanner with a head coil and a pork sample.

Needle Detection

Two experiments were conducted to evaluate the recognition rate and accuracy of needle detection according to an embodiment of the invention. A grid accuracy test was performed to determine distance accuracy by measuring the distance between the detected needle position and the ground truth position. Angular accuracy was also measured in terms of the angular deviation of the reconstructed direction of the needle from the actual needle angle.

Distance Accuracy Test: Experiment Setup

Figure 9:
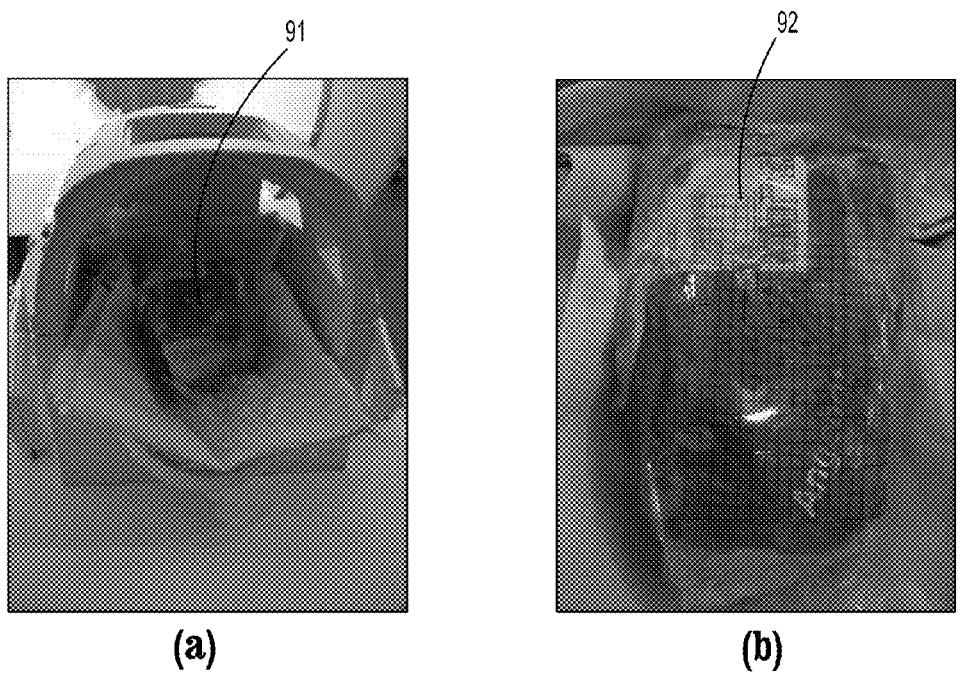
FIG. 9 depicts the experimental setup for a distance accuracy test to validate needle detection, according to an embodiment of the invention.
Figure 10:
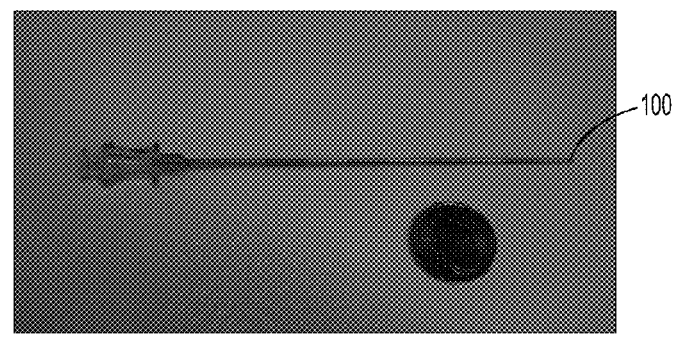
FIG. 10 depicts an MR-compatible 18 Gauge (diameter 1.2 mm) titanium alloy needle with a length of 100 mm that was used for a distance accuracy test, according to an embodiment of the invention.

In this experiment, a transparent foil with an imprinted 5 mm grid was attached to a pork sample, and several entry points were marked for needle insertions. FIGS. 9(a)-(b) depict the experimental setup for the grid accuracy test to validate the detection module. FIG. 9(a) shows a pork sample 91 positioned inside a head coil, and FIG. 9(b) shows the grid 92 with a width of 5 mm attached to the upside of the sample with 12 marked insertion points. A laser used for landmarking the object to be imaged in the MR scanner was utilized for calibration. Landmarking with a laser defines a given position on the object that when moved into the magnet is coincident with the isocenter of the magnet with respect to the scanner coordinate system. Therefore, it is possible to convert the position of the entry points on the grid into the scanner coordinate system by defining a point on the grid using the laser marker. FIG. 10 shows an MR-compatible 18 Gauge (diameter 1.2 mm) titanium alloy needle 100 with a length of 100 mm that was used for the grid accuracy test. The expected needle position for a vertically downward insertion was used as ground truth and was compared to the results of a detection algorithm according to an embodiment of the invention. The needle trajectories for this experiment were perpendicular to the main magnetic field direction, and the needle generated an artifact with a radius of approximately 3 mm. Overall, 12 insertions were performed during real-time image acquisition.

Distance Accuracy Results

The detailed results for this experiment are listed in the table of FIG. 11. The distance of the detected cross section to the ground truth needle position is given as the error in mm and the angular deviation for the reconstructed needle direction is denoted by the error in degrees.

Figures 12, 13:
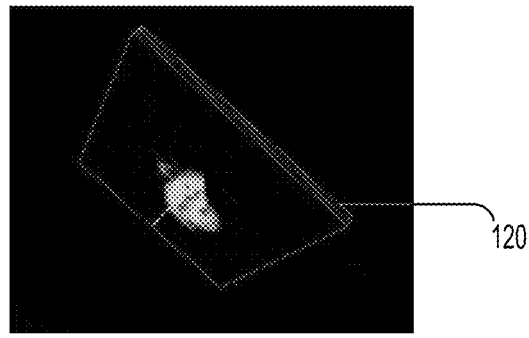
FIG. 12 shows a bounding box overlay used to visualize an identified needle position, and the visible needle artifact, according to an embodiment of the invention.
FIG. 13 is a table of detailed results of a needle detection experiment testing various trajectories with different angles to the main magnetic field direction $B_0$, according to an embodiment of the invention.

All insertions were performed with the three image slices aligned perpendicular to the planned trajectory with a spacing of 7, 14 and 21 mm from the entry point, located on the top of the sample. Detection was visually classified as 'correct' if the bounding box overlay 120 that is used to visualize the identified needle position, as shown in FIG. 12, lies within the visible needle artifact 121, and false otherwise.

The needle artifact was detected correctly in all three image slices for 10 out of 12 insertions. For insertion 9, two cross sections were identified correctly while the artifact was not detected in the first slice. For insertion 10, the artifact was detected correctly in two image slices and incorrectly detected in the first slice. Overall, 34 out of 36 cross-sections were identified correctly, thus resulting in a detection rate of 94%.

To assess the accuracy of the detection module, the distance of the detected needle artifact to the ground truth needle centerline was calculated. For the 34 successful detections, the mean distance was 2.5 mm (median 2.4 mm) with a standard deviation of 1.2 mm. An overview of the detection accuracy for each insertion is given in the "Error [mm]" column of the table of FIG. 11.

Furthermore, as detection will be used to determine an initial needle position, the ground truth needle direction was compared to the reconstructed needle direction. Two approaches were taken based on the number of planes in which the needle artifact was detected. For successful detection of the needle artifact in two out of three image planes, the needle direction was calculated as the direction vector between both positions. When the needle artifact was detected in all three image slices, linear regression was used to fit a straight line through the positions. The residual error was minimized by means of the sum of squared distances. For insertion 10, the '*' in the table of FIG. 11 indicates that the wrong detection was discarded and the orientation was calculated from the two correct detections. For all insertions, the reconstructed needle direction resulted in a mean angular deviation of 7.7° (median 7.1°) with a standard deviation of 3.7°. The detailed direction results are given in the "Error [°]" column of the table of FIG. 11.

The experiment setup itself introduced certain inaccuracies that should be considered when reviewing these results. First, the transparent foil used to mark the entry points could not be attached perfectly planar due to the curved surface of the sample. Second, the manual insertion of the needle by an operator can cause an error regarding the angle of insertion. This is due to the fact that the operator is standing in front of the MR scanner during the experiment and has to reach inside the scanner bore to place the needle. Therefore, it is possible that the true insertion direction has a certain deviation from the ground truth needle direction, which is assumed to have a perfect 90° insertion angle with respect to the grid.

Angular Accuracy Test

As discussed above, the orientation of the needle with respect to the main magnetic field $B_0$ affects the size of the resulting needle artifact. Therefore, in the second experiment, the needle was inserted at different angles to evaluate the detection robustness for different trajectories with respect to the main magnetic field direction.

Experiment Setup

To set up the needle trajectory, a 3-D dataset was acquired prior to the tests and imported into the planning tool. The position of the sample was not changed throughout the entire experiment. The planned trajectory in the 3-D view of the planning tool was displayed for the operator to see while inserting the needle during real-time scanning. Similar to the grid accuracy experiment, the insertions were performed manually, and image slices were acquired perpendicular to the planned trajectory with a spacing of 7, 14 and 21 mm from the entry point. After each insertion, the needle was left in the sample and an additional 3-D dataset was acquired. This dataset was used to extract the ground truth position of the needle artifact by segmenting the needle centerline manually, using the MITK 1 (The Medical Imaging Interaction Toolkit http://www.mitk.org/).

Angular Accuracy Results

Overall, 6 insertions were recorded, and the detailed results of the various trajectories with different angles to the main magnetic field direction $B_0$ are given in the table of FIG. 13. The distance of the detected cross section to the ground truth needle position is given in mm and the angular deviation for the reconstructed needle direction is denoted in degrees.

The needle artifact was correctly detected in all three image slices during 3 insertions. For 2 insertions, the artifact was identified in two slices and not detected in the third slice. During one insertion with the trajectory nearly parallel to the main magnetic field, the needle artifact was not detected at all.

The 13 successful detections of the total 18 detection events resulted in an overall detection rate of 72%. The mean distances of the cross section centroids to the ground truth needle positions are shown in the table of FIG. 13 (reported as "Error [mm]" in the table) with a mean of 1.70 mm (median 0.79 mm) with a standard deviation of 1.71 mm.

To determine the accuracy for detecting the needle direction, the grid test approach was used to reconstruct the needle direction. For the 5 insertions with two or more correctly detected cross sections, the angular deviation of the estimated to the ground truth needle direction was calculated (reported as "Error [°]" in the table) and resulted in a mean of 11.2° (median 13.1°) with a standard deviation of 7.0°.

Figure 14:
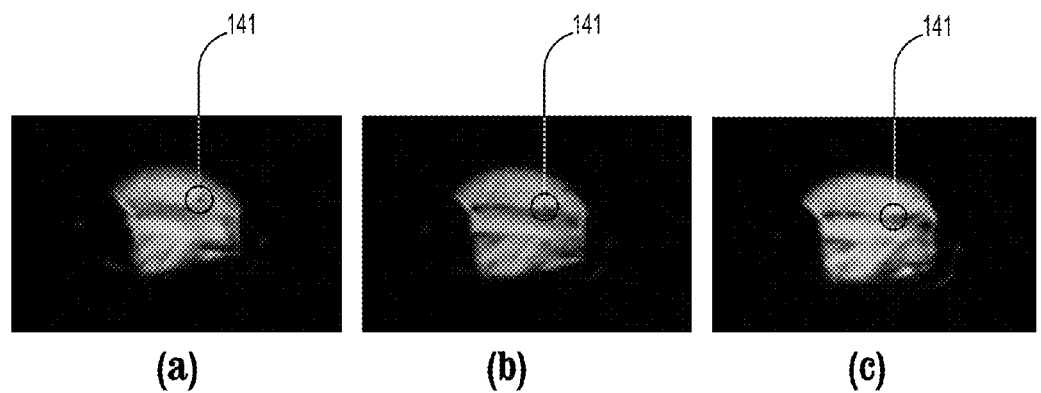
FIGS. 14(a)-(c) depicts three MR images acquired with a barely visible needle artifact, according to an embodiment of the invention.

The missed detections during insertion 5 are due to the small angle between the needle trajectory and the main magnetic field direction. As explained above, the artifact size decreases rapidly as the needle axis approaches the main magnetic field direction. FIGS. 14(a)-(c) shows an example with three slice images and the needle inserted. The needle artifact 141 is still visible in the first image but is barely visible in the two remaining slices. The needle was inserted at a 27.5° angle to the main magnetic field direction and no cross section could be detected due to the small artifact size, shown in FIG. 14(a) as well as the low intensity in surrounding tissue, shown in FIGS. 14(b) and (c). The images are acquired perpendicular to the planned trajectory with distances of 7, 14 and 21 mm from the entry point.

It was observed during this experiment that the operator's hand and corresponding motion artifacts can cause false detections. To resolve this issue and avoid false detections, filtering of candidates based on their distance to the planned trajectory was shown to be effective. Throughout the experiment, the maximum distance for candidate regions to the planned trajectory was set to 30 mm. This value was shown to be suitable for filtering changes in the image caused by the operator's hand, as they are usually further away from the planned path. In addition, the threshold proved to be tolerant enough for smaller deviations occurring during a normal needle insertion.

Another issue that arose during this experiment is that the tissue displacement at the beginning of the insertion can cause false detections. Before the needle penetrates the surface, it compresses the tissue resulting in increased signal intensities near the entry point. This effect was clearly visible in the real-time images, especially in the slice acquired closest to the entry point. In contrast to the needle artifact causing an immediate intensity change, this effect exhibited a gradual increase in the image intensities. The background subtraction algorithm in combination with the applied thresholding has proven to be adequate for compensating this effect.

Needle Tracking

In the following, an evaluation of needle tracking according to an embodiment of the invention is presented. Real-time image acquisition was simulated using a 4-D MRI dataset acquired during needle insertion into a sample. Tracking was achieved by iteratively applying a model fitting algorithm according to an embodiment of the invention for every time step in the 4-D dataset where the image slices were automatically realigned with respect to the current needle position.

Data Acquisition and Simulation

The 4-D dataset comprised 16 3-D datasets that were acquired during needle insertion into a pork sample using a 3-D-FLASH sequence. The sample was positioned in the scanner and the first dataset was acquired without the needle inserted. For the subsequent acquisitions the sample remained in the same position and the needle was inserted approximately 5 mm between the scans, until an insertion depth of about 75 mm was reached. Each dataset included 52 images with 2 mm thickness, an in-plane resolution of 192× 156 pixels and an equidistant pixel spacing of 1.6 mm. These individual datasets were merged into one 4-D dataset and used to simulate real-time imaging. An application that simulates image acquisition with a real MR scanner using a BEAT sequence was used to generate three image slices for every time step of the 4-D dataset.

Figure 15:
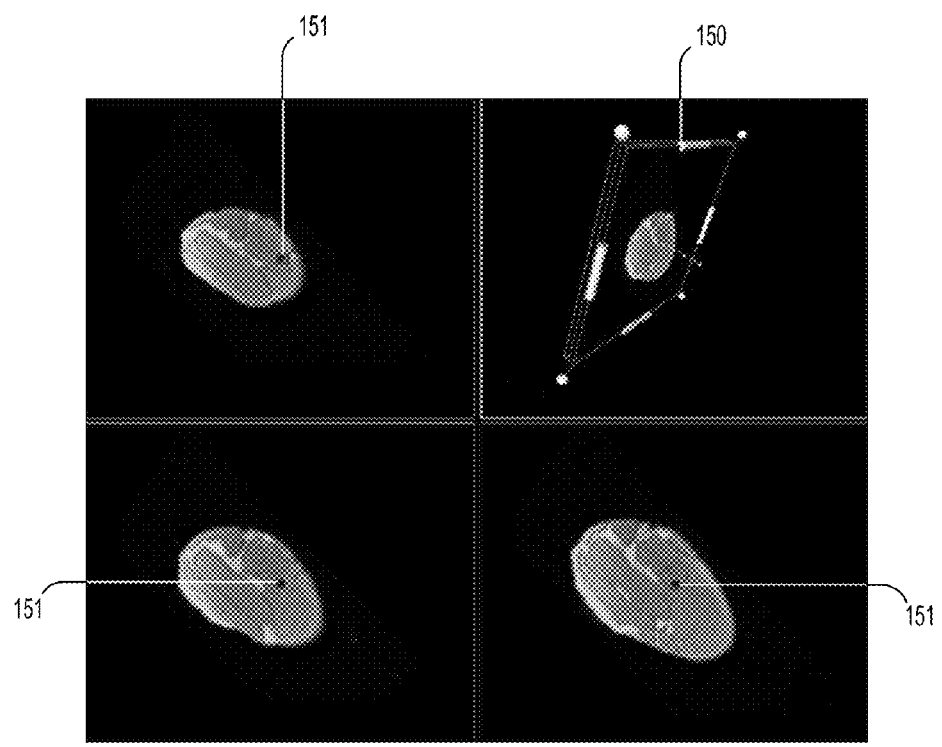
FIG. 15 shows identified artifact cross sections for a needle tracking simulation, according to an embodiment of the invention.

To simulate needle tracking during a real procedure, a needle trajectory was planned using the 3-D dataset without the needle inserted and the initial needle position was reconstructed using a detection module according to an embodiment of the invention. FIG. 15 shows the trajectory 150 and the successfully detected artifact cross sections 151. The slices were aligned perpendicular to the planned trajectory with a spacing of 7, 14 and 21 mm from the entry point. In the fifth time step the needle artifact was identified in all three image slices and linear regression was used to reconstruct the needle direction based on the three detected needle artifact positions. The base point of the needle was set to the intersection of the reconstructed centerline with the image plane at distance 7 mm from the entry point. A needle tip modeled by the direction vector was set to the intersection of the centerline with the third image plane at distance 21 mm. This needle position was used to initialize a tracking algorithm according to an embodiment of the invention.

Figures 16, 17:
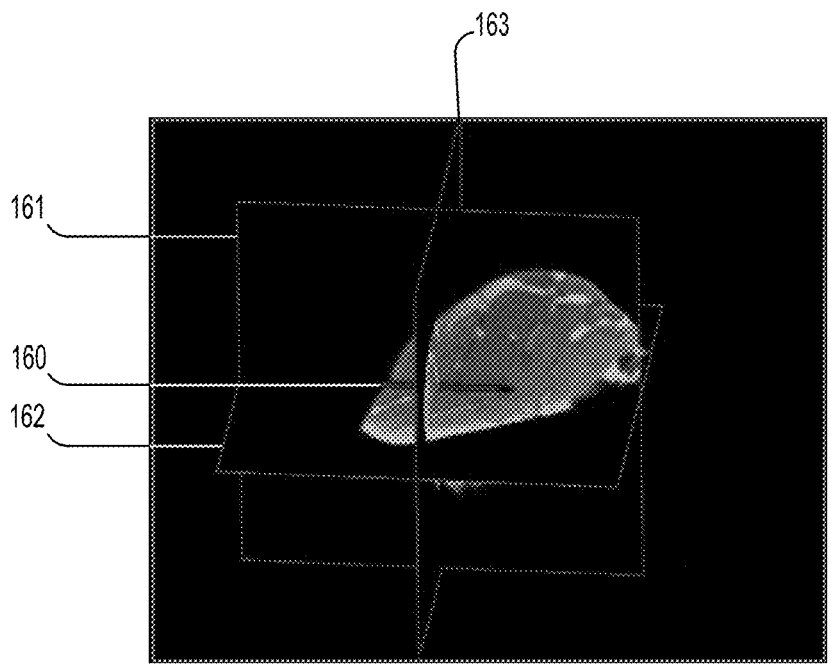
FIG. 16 illustrates an imaging strategy for testing needle tracking, according to an embodiment of the invention.
FIG. 17 is a table of detailed results for a needle tracking simulation, according to an embodiment of the invention.

According to an embodiment of the invention, needle tracking was simulated in a two-step process. First, the three image slices were acquired with respect to the current needle position. An imaging strategy used to dynamically realign the image slices is shown in FIG. 16. After each time step, the slices are positioned with respect to the current needle position, visualized as a cylinder 160. Two images 161, 162 were acquired parallel to the needle and perpendicular to each other, showing a longitudinal section. The third slice 163 was positioned perpendicular to the needle axis at the needle center, exhibiting an artifact cross section. The images were reconstructed during the simulation from the 4-D dataset with a resolution of 156×156 pixels. Next, this image information was used to perform a best neighbor optimization and obtain a new estimate for the needle position. The needle artifact radius was set to 2.75 mm and the stepsize of the best neighbor optimizer was initialized to 4 mm with a minimum of 0.1 mm to terminate the optimization.

Needle Tracking Results

The detailed results for this experiment are presented in the table of FIG. 17. The needle tracking was started in the 5th time step after the detection was finished and an initial needle position was available. The distance of the model tip to the true needle tip position is given in mm and the angular deviation of the model direction to the true needle direction is denoted in degrees. For every time step the ground truth position of the needle was extracted by manual segmentation of the needle centerline in the corresponding 3-D dataset.

The insertion depth of the needle (reported as "Needle [mm]") and the length of the needle model (reported as "Model [mm]") are given in mm for every time step in the table of FIG. 17. The number in the "Iterations" column indicates the number of steps needed until no lower value of the cost function could be found using the best neighbor optimization strategy. This can be employed to assess the performance of the needle tracking. Every iteration during optimization required 12 evaluations of the cost function and took approximately 140 ms on a Dual Core1.66 Ghz system with 1024 MB RAM running Windows XP (SP3). For the 12 individual optimizations, an average of 24.6 iterations was required, resulting in a mean computation time of 3.4 seconds.

To evaluate the accuracy of a model fitting approach according to an embodiment of the invention, the Euclidean distance of the ground truth needle to the model tip position was calculated for every time step. These distances are reported as "Error [mm]" in the table of FIG. 17. The mean Error over the 12 time steps was 2.3 mm (median 2.2 mm) with a standard deviation of 1.4 mm. Similarly, the angular deviation was calculated using the estimated direction of the needle model and the ground truth needle direction for every time step. These deviations are reported as "Error [°]" in the table of FIG. 17. The mean angular deviation over the 12 time steps was 1.8° (median)1.8° and a standard deviation of 0.8°.

During development and testing, two issues emerged concerning an image-based tracking approach according to an embodiment of the invention. One issue concerns the robustness of the model fitting, as the estimated needle position is used to dynamically align the image slices. Therefore, an incorrect localization of the needle propagates and leads to consecutive errors and false needle localization. Approaches for enhancing robustness are based on either adding constraints for the needle location or incorporating additional image characteristic information. These constraints can apply to the general needle position, as well as the motion of a needle during the insertion. With the planned trajectory available, it is possible to validate the location of the needle during the procedure and therefore identify unlikely needle positions. In addition, the motion of the needle during a procedure can be modeled, for example by constraining the possible locations of the needle tip and angular movement over time, i.e. between subsequent image frames. It can also be taken into consideration that the needle entry point is subject to considerably less movement during the intervention than the needle tip. Combining these constraints has the potential to reduce the search space and improve the accuracy and robustness of a tracking module according to an embodiment of the invention. In addition, assuming that no motion occurs between the planning and the actual procedure, the pre-acquired high resolution 3-D data set used in the planning tool could also be used to aid tracking or just provide additional information to the physician. MPR images can be extracted from the 3-D dataset corresponding to the same slice positions as the real-time images. Although image contrast and spatial resolution differ between the two images, strategies could be developed to use an image comparison to support needle tracking. Such strategies may include 2-D/3-D image registration, signal normalization, and edge detection.

Figure 18:
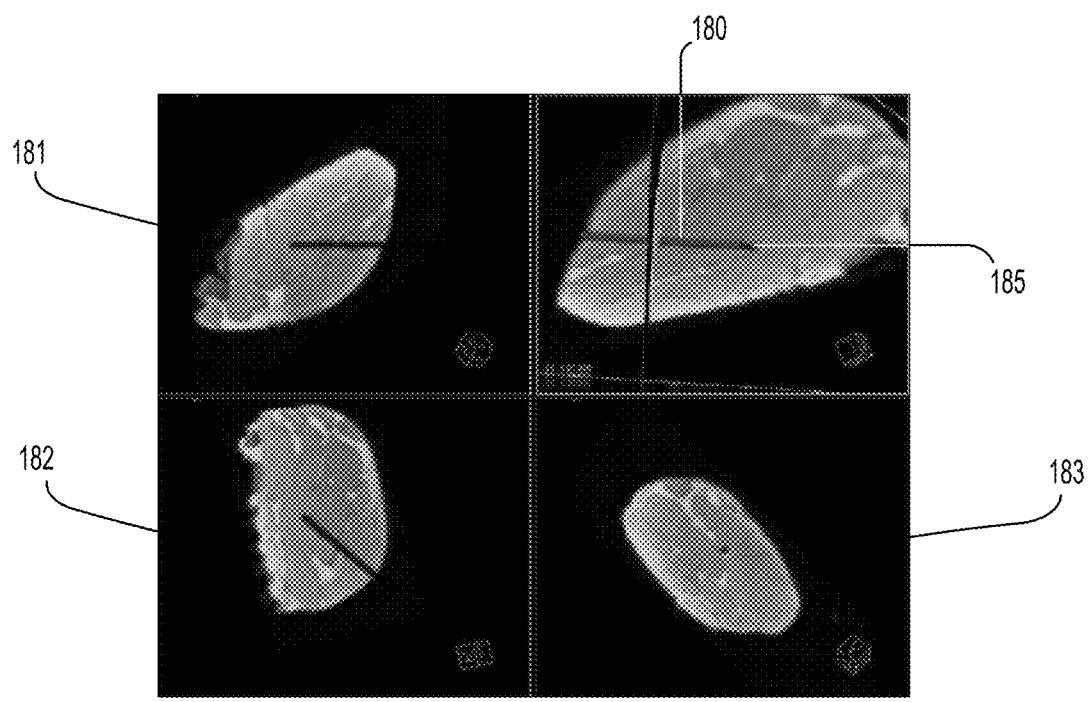
FIG. 18 shows the final position of a needle model together with the image slices acquired for this iteration, according to an embodiment of the invention.

A second issue involves the convergence of the model towards the needle tip. In several tests, a model according to an embodiment of the invention converged to the true needle position but did not extend to the full length of the artifact. This effect occurred during the time steps 13-16 of the simulation and is indicated by the distance of the model tip position to the ground truth needle tip location given in the "Error [mm]" column of the table of FIG. 17. Beginning from time frame 13, this error increased until it reached 5.9 mm after the last iteration. In FIG. 18, the final position of the needle model 180 is shown after the 16$^{th}$ timestep together with the image slices 181, 182, 183, acquired for this iteration. The screenshot shows that the needle model converged to the correct needle artifact 185 but did not extend to its full length. This shortcoming occurs as a result of the parameterization of the needle model. A possible solution is to employ a different parameterization corresponding to a more suitable shape of the cost function to be optimized. For example, instead of using a base point and a no normalized direction vector, the needle direction and length could be represented in spherical coordinates with the base point as the origin. That is, the needle direction is given by the azimuth angle and the elevation angle, whereas the needle length is encoded by the radial distance. Thus, the needle model still has six degrees of freedom. Moreover, since length is encoded independent of direction, this parameter space might be more adequate for representing the movement of the needle during insertion.

System Implementation

It is to be understood that embodiments of the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 19:
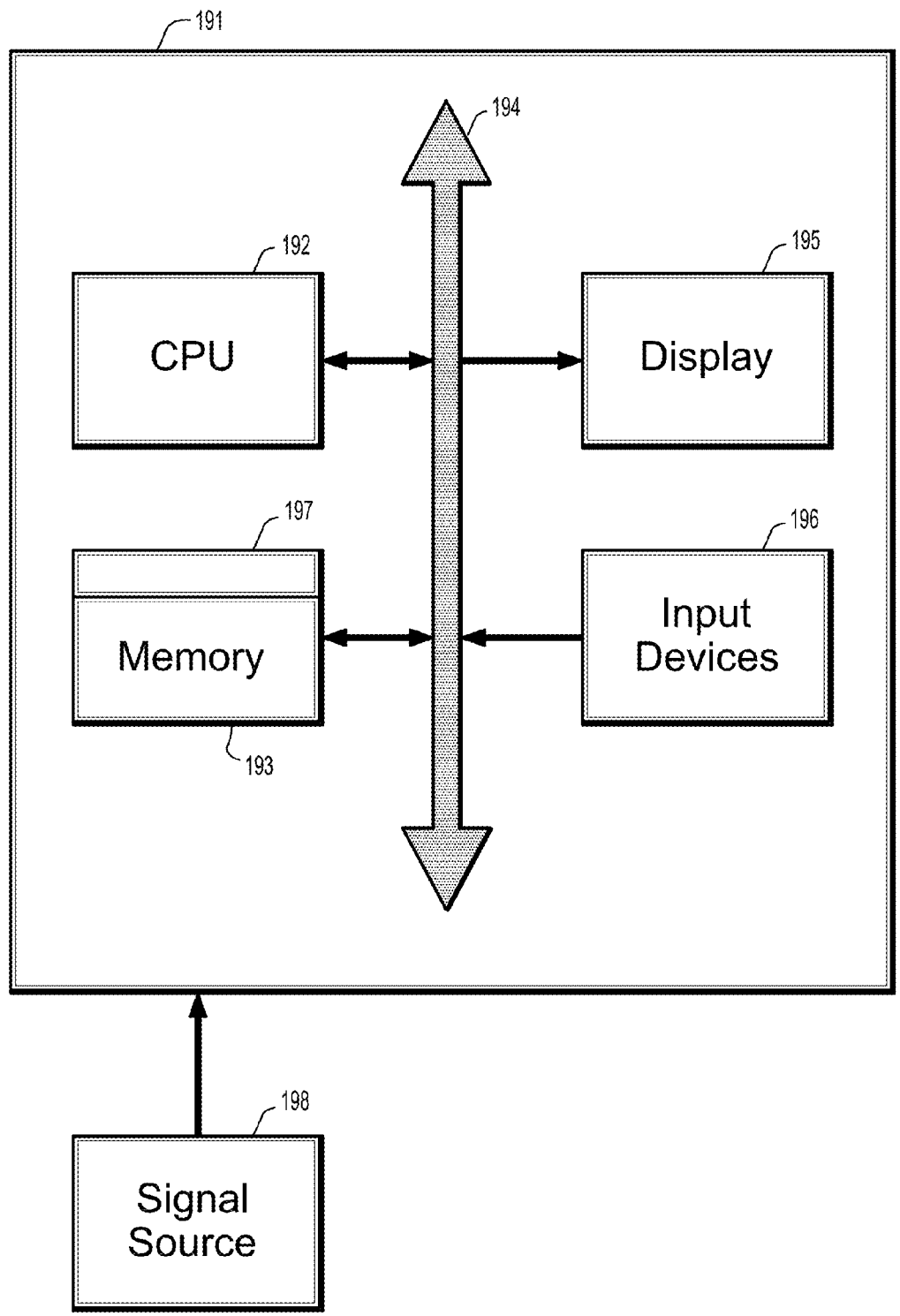
FIG. 19 is a block diagram of an exemplary computer system for implementing a method for passive needle guidance during MRI guided procedures using only image intensity information, according to an embodiment of the invention.

FIG. 19 is a block diagram of an exemplary computer system for implementing a method for passive needle guidance during MRI guided procedures using only image intensity information, according to an embodiment of the invention. Referring now to FIG. 19, a computer system 191 for implementing the present invention can comprise, inter alia, a central processing unit (CPU) 192, a memory 193 and an input/output (I/O) interface 194. The computer system 191 is generally coupled through the I/O interface 194 to a display 195 and various input devices 196 such as a mouse and a keyboard. The support circuits can include circuits such as cache, power supplies, clock circuits, and a communication bus. The memory 193 can include random access memory (RAM), read only memory (ROM), disk drive, tape drive, etc., or a combinations thereof. The present invention can be implemented as a routine 197 that is stored in memory 193 and executed by the CPU 192 to process the signal from the signal source 198. As such, the computer system 191 is a general purpose computer system that becomes a specific purpose computer system when executing the routine 197 of the present invention.

The computer system 191 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to exemplary embodiments, those skilled in the art will appreciate that various modifications and substitutions can be made thereto without departing from the spirit and scope of the invention as set forth in the appended claims.

What is claimed is:

1. A method for tracking a needle along a path under real-time magnetic resonance imaging (MRI) guidance, comprising the steps of:
    extracting a candidate needle artifact region from a plurality of incoming MR images of a needle inside biological tissue;
    determining an initial needle direction vector from the candidate needle artifact region in each of the plurality of incoming needle images;
    determining an initial needle base point from an intersection of the needle direction vector with a first incoming needle image, and an initial needle tip point from an intersection of the needle direction vector with a last incoming needle image; and
    tracking said needle by minimizing a cost function of the initial base point and initial direction vector to calculate an updated base point and updated direction vector, wherein the updated base point and direction vector are used to visualize the advance of the needle along the path through the biological tissue.

2. The method of claim 1, wherein extracting candidate needle artifact regions comprises:
    receiving a current MR needle image defined as an MR image containing the needle artifact;
    extracting a plurality of pixel regions from the current MR needle image having a lower image intensity than surrounding pixels;
    calculating a plurality of features for each pixel region; and
    selecting one or more pixel regions, based on the features of each region, that are likely to represent a needle artifact, as candidate needle artifact regions,
    wherein, if more than one pixel region is selected, choosing a region closest to the path as the candidate needle artifact region.

3. The method of claim 2, wherein the plurality of pixel regions are extracted from the current MR needle image by subtracting the current MR needle image from a background model, extracting those pixels whose intensity difference with respect to corresponding pixels in the background model is greater than a predetermined threshold, and using connected-component analysis to form pixel regions from the extracted pixels.

4. The method of claim 3, wherein a pixel i is extracted if the intensity difference $E_t(x_i) - I_t(x_i) \geq d_{threshold}$, wherein $E_t$ is the background model, $I_t$ is the current image, and $x_i$ is the position of pixel i.

5. The method of claim 3, further comprising, if no region is selected as a candidate needle artifact region, updating the background model with the current image.

6. The method of claim 2, wherein features calculated for the extracted pixel regions include an area, a perimeter, a circularity, a centroid, and a distance from the centroid to the planned path, wherein regions whose centroid is less than a predetermined distance from the planned path, whose circularity is less than a predetermined maximum, and whose area is within a predetermined range, are selected as candidate needle artifact regions.

7. The method of claim 1, wherein said cost function of the base point and direction vector is given by $$J(b, d) = \sum_{i=0}^{N} I_i w_k(k(x_i, b, d)) w_l(l(x_i, b, d)) \in R,$$

wherein base point $b = (b_x, b_y, b_z)^T \in R^3$, direction vector $d = (d_x, d_y, d_z)^T \in R^3$, $x_i$ is the position of pixel i, $I_i$ is the image intensity for pixel i, N is the number of pixels, $w_k$ is given by $$w_k(k(x,b,d)) = H(k(x,b,d))H(1-k(x,b,d)),$$

where H is the Heaviside step function and k is given by $$k(x, b, d) = \frac{(x-b)^T d}{\|d\|^2} \in R,$$

$w_l$ is given by $$w_l(l(x, b, d)) = N(l(x, b, d), \mu_1, \sigma_1) - \frac{1}{2} N(l(x, b, d), \mu_2, \sigma_2),$$

wherein l is given by $$l(x, b, d) = \frac{1}{r} \|p(x, b, d) - x\| \in R,$$

$p(x, b, d) = b + k(x,b,d) d \in R^3$, and $N(x, \mu, \sigma)$ denotes the probability density function for a univariate normal distribution with the mean $\mu$ and standard deviation $\sigma$.

8. The method of claim 7, wherein minimizing said cost function comprises acquiring at least three images with respect to a current needle position, wherein at least two images are parallel to the needle and perpendicular to each other, and the third image is perpendicular to longitudinal axis of the needle, and minimizing said cost function in said images to obtain a new needle position.

9. The method of claim 7, wherein minimizing said cost function comprises updating a parameter vector p=(b, d) according to $$p_{i+1} = \underset{p \in N_i}{\operatorname{argmin}} J(p)$$

wherein $N_i$ is a neighborhood about p generated for each iteration i by varying the vector p by a stepsize$\pm \gamma_{BN}$ in each dimension.

10. The method of claim 7, wherein minimizing said cost function comprises updating a parameter vector p=(b, d) according to $p_{i+1}=p_i-\gamma_{GD}\nabla J(p_i)$, where $\gamma_{GD}$ denotes a step size.

11. A method for tracking a needle along a path under real-time magnetic resonance imaging (MRI) guidance, comprising the steps of:
 determining an initial base point and an initial direction vector of a needle during an MRI guided intervention by analyzing a needle artifact region in each of a plurality of incoming MR images; and
 tracking said needle during said intervention by minimizing a cost function of the initial base point and initial direction vector to calculate an updated base point and updated direction vector, wherein said cost function of the base point and direction vector is given by $$J(b, d) = \sum_{i=0}^{N} I_i w_k(k(x_i, b, d)) w_l(l(x_i, b, d)) \in R,$$

wherein base point b=$(b_x, b_y, b_z)^T \in R^3$, direction vector d=$(d_x, d_y, d_z)^T \in R^3$, $x_i$ is the position of pixel i, $I_i$ is the image intensity for pixel i, N is the number of pixels, $w_k$ is given by $$w_k(k(x,b,d))=H(k(x,b,d))H(1-k(x,b,d)),$$

where H is the Heaviside step function and k is given by $$k(x, b, d) = \frac{(x-b)^T d}{\|d\|^2} \in R,$$

$w_l$ is given by $$w_l(l(x, b, d)) = N(l(x, b, d), \mu_1, \sigma_1) - \frac{1}{2} N(l(x, b, d), \mu_2, \sigma_2),$$

wherein l is given by $$l(x, b, d) = \frac{1}{r}\|p(x, b, d) - x\| \in R,$$

p(x,b,d)=b+k(x,b,d)d$\in R^3$, and N(x, μ, σ) denotes the probability density function for a univariate normal distribution with the mean μ and standard deviation σ, wherein the updated base point and direction vector are used to advance the needle along the path through biological tissue.

12. The method of claim 11, wherein determining an initial base point and an initial direction vector of a needle comprises:
 receiving a current MR needle image;
 extracting a plurality of pixel regions from the current MR needle image having a lower image intensity than surrounding pixels;
 calculating a plurality of features for each pixel region; and
 selecting one or more pixel regions, based on the features of each region, that are likely to represent a needle artifact, as needle artifact regions,
 wherein, if more than one pixel region is selected, choosing a region closest to the path as the needle artifact region.

13. The method of claim 12, wherein determining a base point and a direction vector of a needle comprises:
 determining an initial needle direction vector from the needle artifact region in each of the plurality of incoming MR images; and
 determining an initial needle base point from an intersection of the needle direction vector with a first incoming MR image, and an initial needle tip point from an intersection of the needle direction vector with a last incoming MR image.

14. A program storage device readable by a computer, tangibly embodying a program of instructions executable by the computer to perform the method steps for tracking a needle along a path under real-time magnetic resonance imaging (MRI) guidance, the method comprising the steps of:
 extracting a candidate needle artifact region from a plurality of incoming MR images of a needle inside biological tissue;
 determining an initial needle direction vector from the candidate needle artifact region in each of the plurality of incoming needle images;
 determining an initial needle base point from an intersection of the needle direction vector with a first incoming needle image, and an initial needle tip point from an intersection of the needle direction vector with a last incoming needle image; and
 tracking said needle by minimizing a cost function of the initial base point and initial direction vector to calculate an updated base point and updated direction vector, wherein the updated base point and direction vector are used to visualize the advance of the needle along the path through the biological tissue.

15. The computer readable program storage device of claim 14, wherein extracting candidate needle artifact regions comprises:
 receiving a current MR needle image defined as an MR image containing the needle artifact;
 extracting a plurality of pixel regions from the current MR needle image having a lower image intensity than surrounding pixels;
 calculating a plurality of features for each pixel region; and
 selecting one or more pixel regions, based on the features of each region, that are likely to represent a needle artifact, as candidate needle artifact regions,
 wherein, if more than one pixel region is selected, choosing a region closest to the path as the candidate needle artifact region.

16. The computer readable program storage device of claim 15, wherein the plurality of pixel regions are extracted from the current MR needle image by subtracting the current MR needle image from a background model, extracting those pixels whose intensity difference with respect to corresponding pixels in the background model is greater than a predetermined threshold, and using connected-component analysis to form pixel regions from the extracted pixels.

17. The computer readable program storage device of claim 16, wherein a pixel i is extracted if the intensity difference $E_t(x_i)-I_t(x_i) \geq d_{threshold}$, wherein $E_t$ is the background model, $I_t$ is the current image, and $x_i$ is the position of pixel i.

18. The computer readable program storage device of claim 16, the method further comprising, if no region is selected as a candidate needle artifact region, updating the background model with the current image.

19. The computer readable program storage device of claim 15, wherein features calculated for the extracted pixel regions include an area, a perimeter, a circularity, a centroid, and a distance from the centroid to the planned path, wherein regions whose centroid is less than a predetermined distance from the planned path, whose circularity is less than a predetermined maximum, and whose area is within a predetermined range, are selected as candidate needle artifact regions.

20. The computer readable program storage device of claim 14, wherein said cost function of the base point and direction vector is given by $$J(b, d) = \sum_{i=0}^{N} I_i w_k(k(x_i, b, d)) w_l(l(x_i, b, d)) \in R,$$

wherein base point $b=(b_x, b_y, b_z)^T \in R^3$, direction vector $d=(d_x, d_y, d_z)^T \in R^3$, $x_i$ is the position of pixel i, $I_i$ is the image intensity for pixel i, N is the number of pixels, $w_k$ is given by $$w_k(k(x,b,d)) = H(k(x,b,d))H(1-k(x,b,d)),$$

where H is the Heaviside step function and k is given by $$k(x, b, d) = \frac{(x-b)^T d}{\|d\|^2} \in R,$$

$w_l$ is given by $$w_l(l(x, b, d)) = N(l(x, b, d), \mu_1, \sigma_1) - \frac{1}{2} N(l(x, b, d), \mu_2, \sigma_2),$$

wherein l is given by $$l(x, b, d) = \frac{1}{r} \|p(x, b, d) - x\| \in R,$$

$p(x,b,d)=b+k(x,b,d)d \in R^3$, and $N(x, \mu, \sigma)$ denotes the probability density function for a univariate normal distribution with the mean $\mu$ and standard deviation $\sigma$.

21. The computer readable program storage device of claim 20, wherein minimizing said cost function comprises acquiring at least three images with respect to a current needle position, wherein at least two images are parallel to the needle and perpendicular to each other, and the third image is perpendicular to longitudinal axis of the needle, and minimizing said cost function in said images to obtain a new needle position.

22. The computer readable program storage device of claim 20, wherein minimizing said cost function comprises updating a parameter vector p=(b, d) according to $$p_{i+1} = \underset{p \in N_i}{\arg\min} J(p)$$

wherein $N_i$ is a neighborhood about p generated for each iteration i by varying the vector p by a stepsize$\pm \gamma_{BN}$ in each dimension.

23. The computer readable program storage device of claim 20, wherein minimizing said cost function comprises updating a parameter vector p=(b, d) according to $p_{i+1}=p_i-\gamma_{GD} \nabla J(p_i)$ where $\gamma_{GD}$ denotes a step size.

* * * * *